United States Patent
Jayaraman et al.

(10) Patent No.: US 12,428,464 B2
(45) Date of Patent: Sep. 30, 2025

(54) STABLE FUSION PROTEIN FORMULATION

(71) Applicant: DR. REDDY'S LABORATORIES LIMITED, Hyderabad (IN)

(72) Inventors: Murali Jayaraman, Kancheepuram (IN); Lakshmi Kanakadurga M, Hyderabad (IN)

(73) Assignee: DR. REDDY'S LABORATORIES LIMITED, Hyderabad (IN)

( * ) Notice: Subject to any disclaimer, the term of this patent is extended or adjusted under 35 U.S.C. 154(b) by 1049 days.

(21) Appl. No.: 17/058,190

(22) PCT Filed: May 24, 2019

(86) PCT No.: PCT/IN2019/050408
§ 371 (c)(1),
(2) Date: Nov. 24, 2020

(87) PCT Pub. No.: WO2019/224842
PCT Pub. Date: Nov. 28, 2019

(65) Prior Publication Data
US 2021/0188941 A1    Jun. 24, 2021

(30) Foreign Application Priority Data
May 25, 2018   (IN) .............................. 201841019605

(51) Int. Cl.
*C07K 14/705*   (2006.01)
*C07K 1/34*   (2006.01)

(52) U.S. Cl.
CPC .......... *C07K 14/70521* (2013.01); *C07K 1/34* (2013.01); *C07K 2319/30* (2013.01)

(58) Field of Classification Search
CPC ............ C07K 2319/30; C07K 2319/32; C07K 14/70521; A61K 47/183; A61K 47/26
See application file for complete search history.

(56) References Cited

U.S. PATENT DOCUMENTS

| | | |
|---|---|---|
| 8,642,557 B2 | 2/2014 | Akamatsu et al. |
| 10,450,361 B2 | 10/2019 | Robblee et al. |
| 2010/0166774 A1 | 7/2010 | Dali et al. |
| 2019/0092836 A1 | 3/2019 | Leister et al. |

FOREIGN PATENT DOCUMENTS

| | | | |
|---|---|---|---|
| CN | 101199484 B | 8/2011 | |
| WO | WO-9312812 A1 * | 7/1993 | ............. A61K 38/27 |
| WO | WO-2007076354 A2 * | 7/2007 | ......... A61K 38/1774 |
| WO | 2009/053358 A1 | 4/2009 | |
| WO | WO-2018204368 A1 * | 11/2018 | ......... A61K 39/3955 |

OTHER PUBLICATIONS

International Search Report dated Jul. 24, 2019, for corresponding International Patent Application No. PCT/IN2019/050408.
Written Opinion dated Jul. 24, 2019, for corresponding International Patent Application No. PCT/IN2019/050408.
International Search Report dated Jul. 25, 2019, for related International Patent Application No. PCT/IN2019/050409.
Written Opinion dated Jul. 25, 2019, for corresponding International Patent Application No. PCT/IN2019/050409.

* cited by examiner

*Primary Examiner* — Karen A. Canella
(74) *Attorney, Agent, or Firm* — PERGAMENT & CEPEDA LLP

(57) ABSTRACT

The present invention discloses a stable pharmaceutical formulation of a fusion protein, wherein the formulation contains buffer, sugar, amino acid and surfactant, and optionally includes salts. The disclosed fusion protein formulations are liquid formulations that are also suitable for lyophilization.

2 Claims, No Drawings

STABLE FUSION PROTEIN FORMULATION

This application is a National Stage Application under 35 U.S.C. § 371 of PCT International Application No. PCT/IN2019/050408, filed May 24, 2019, which claims the benefit of Indian provisional patent application No. 201841019605 filed on May 25, 2018, all of which are herein incorporated by reference in their entireties.

FIELD OF INVENTION

The present invention is related to stable formulation of a fusion protein molecule. In particular, the invention discloses stable cytotoxic T-lymphocyte-associated protein 4-immunoglobulin (CTLA4-Ig) fusion protein formulation, wherein the formulation comprises buffer systems and stabilizers.

BACKGROUND

Over the past two decades, recombinant DNA technology has led to the commercialization of many proteins, particularly antibody therapeutics and fusion protein molecules.

Fusion proteins, in particular, Fc fusion protein molecules (in which Fc portion of human immunoglobulin (Ig) is conjugated to a particular portion of a receptor) are gaining significance, since their wide usage in treatment of various oncological and immunological disorders. Etanercept (TNFR-IgFc), aflibercept (VEGFR-IgFc) and abatacept and belatacept (CTLA4-IgFc) are among those Fc fusion proteins approved by Food and Drug Administration (FDA) to treat various disorders. The effectiveness of fusion protein molecule is majorly dependent on the stability, route of administration and their dosage forms and concentrations. This in turn, necessitates these protein molecules to be formulated appropriately to retain stability and activity.

Proteins in general, and Fc fusion proteins in particular, are typically unstable in solution and sensitive to pH, temperature and oxidation and hence can undergo a variety of covalent and non-covalent reactions, modifications or degradations in solution. The more common protein degradation pathways include aggregation, deamidation and/or oxidation and these degradation pathways are known to be influenced by pH, temperature and storage conditions, including formulation conditions and excipients. These pathways thus lead to both physical and chemical instability of a protein in solution.

Aggregation in therapeutic proteins, is of particular interest, because it often results in decreased bioactivity/loss of activity over a period of time and may be immunogenic when administered to a patient. In case of fusion proteins aggregation is significant since they involve fusion of two or more proteins, are large and complex structure and tend to form aggregates at a rapid rate as compared to simple polypeptides or antibodies.

Apart from aggregation, another type of instability of a multimeric protein, specifically occurring at the regions where two or more proteins are fused, is fragmentation/clipping which can be a result of deamidation, oxidation, isomerization and/or hydrolysis. Deamidation can occur at asparagine or glutamine residues, resulting in a charge variant/s of the protein. Oxidation of fusion proteins involves mainly methionine residues, and are generally influenced by external factors such as exposure to light and transition metal ions or degradation product of an excipient (e.g., hydrogen peroxide from polysorbate degradation). Presence of these oxidized products and charge variants in a therapeutic protein molecule are known to increase instability and, thus decrease the bioactivity of the protein.

Hence, it is essential to develop a suitable mixture of formulation component/s that would stabilize a therapeutic (fusion) protein molecule against the many physical and chemical instability inducing factors. Further, the developed formulation should maintain colloidal stability during storage conditions, since it measures and ensures that the protein molecules remain suspended in an aqueous solution at equilibrium.

There are numerous class of excipients such as sugars (sugar or sugar alcohols), amino acids and surfactants which are used in stabilizing proteins and fusion protein molecules. However, the choice of excipients while formulating a protein is governed by various other factors such as their compatibility with the protein and other components in the formulation, (intended) mode of administration and dosage of the therapeutic protein, etc. Therefore, the challenge behind a formulation development involves screening and selection of suitable buffer conditions and excipients, including their concentrations, to achieve a stable formulation. Further, it is also expected that the developed formulation is stable at room temperature and be suitable to be administered in either lyophilized or liquid form.

SUMMARY

The present invention discloses a stable pharmaceutical formulation of a fusion protein molecule comprising buffer, sugar, amino acid and surfactant, wherein the fusion protein is a CTLA4-Ig molecule.

In particular, the invention discloses a stable pharmaceutical formulation of CTLA4-Ig fusion protein comprising buffer, sugar, amino acid and surfactant, wherein the said formulation optionally contains pharmaceutically acceptable excipients such as salts.

In addition, the invention discloses a method of reducing aggregation and/or fragmentation of CTLA4-Ig fusion protein by formulating in a formulation comprising amino acid and sugar. More specifically, the invention comprises a CTLA4-Ig fusion protein formulation stabilized by the combination of histidine and sugar. This combination of sugar and histidine imparts colloidal stability to the fusion protein molecule present in the formulation.

Also and particularly, the inventive formulation is devoid of arginine or lysine or glycine or methionine; or does not require/include any other amino acids, other than histidine, that are commonly used as stabilizers in therapeutic protein formulation.

In addition, the invention also discloses a method of increasing the stability of CTLA4-Ig fusion protein formulation, comprising histidine and sugar, wherein the histidine and sugar components are also added during the process step i.e., in particular in the tangential flow filtration process step (a step before the formulation step). Such addition during the process imparts significant stability to the formulation.

The CTLA4-Ig fusion protein in the said formulation is stable at lower, as well as, higher concentrations (from 10 mg/ml to 200 mg/ml) at various temperatures. The formulation is stable for at least four weeks when stored at 25° C., or for at least two weeks at 30° C., and contains less than 10% of the protein molecule in aggregate form.

DETAILED DESCRIPTION OF THE INVENTION

Definitions

The term "fusion protein" means a protein formed by fusing (i.e., joining) all or part of two polypeptides which are not the same. Typically, fusion proteins are made using recombinant DNA techniques, by end to end joining of polynucleotides encoding the two polypeptides.

The terms "CTLA4-Ig" or "CTLA4-Ig molecule" or "CTLA4Ig molecule" are used interchangeably, and refer to a protein molecule that comprises a polypeptide having a CTLA4 extracellular domain or a portion thereof, and an immunoglobulin constant region or a portion thereof. The extracellular domain and the immunoglobulin constant region can be wild-type, or mutant or modified, and mammalian, including human or mouse. The polypeptide can further comprise additional protein domains. A CTLA4-Ig molecule can also refer to multimer forms of the polypeptide, such as dimers, tetramers, and hexamers. A CTLA4-Ig molecule also is capable of binding to CD80 and/or CD86.

The term "stable" formulation refers to the formulation wherein the antibody therein retains its physical stability and/or chemical stability and/or biological activity, upon storage.

Pre-formulation steps refer to any or multiple steps performed before formulating the protein into a therapeutic product. Examples of such steps include, chromatography, filtration, (ultrafiltration, sterile filtration, nano filtration, diafiltration, depth filtration), or any other steps performed to concentrate the protein or to exchange the buffer to a different/suitable buffer. The filtration steps mentioned herein may be performed in a tangential flow filtration mode.

Stability studies provides evidence of the quality of an antibody under the influence of various environmental factors during the course of time. ICH's "Q1A: Stability Testing of New Drug Substances and Products," states that data from accelerated stability studies can be used to evaluate the effect of short-term excursions higher or lower than label storage conditions that may occur during the shipping of the antibodies.

Various analytical methods are available for measuring the physical and chemical degradation of the fusion protein in the pharmaceutical formulations. A fusion protein "retains its physical stability" in a pharmaceutical formulation if it shows substantially no signs of aggregation, precipitation and/or denaturation upon visual examination of color and/or clarity, or as measured by UV light scattering or by size exclusion chromatography. A fusion protein is said to "retain its chemical stability" in a pharmaceutical formulation when its shows no or minimal formation of product variants which may include variants as a result of chemical modification of fusion protein such as deamination, oxidation etc. Analytical methods such as ion exchange chromatography and hydrophobic ion chromatography may be used to investigate the chemical product variants.

The monomer, dimer and high molecular weight (HMW) species of CTLA4Ig molecule may be separated by size exclusion chromatography (SEC). SEC separates molecules based on the molecular size. Separation is achieved by the differential molecular exclusion or inclusion as the molecules migrate along the length of the column. Thus, resolution increases as a function of column length. In order to maintain the appropriate activity of a fusion protein, it is desirable to reduce the formation of aggregate or fragmentation (monomer/low molecular weight species) of products and hence control the dimer content to a target value. Dimer is major form present in fusion proteins and elutes as main peak in size exclusion chromatography. CTLA4Ig molecule samples may be separated using a 2695 Alliance HPLC (Waters, Milford, Mass.) equipped with TSK Gel® G3000SWXL (300 mm×7.8 mm) and TSK Gel® G3000SWXL (40 mm×6.0 mm) columns (Tosoh Bioscience, Montgomery, Pa.).

The colloidal stability of a protein gives information on interaction of proteins molecules within self, and between the surrounding molecules, in an aqueous environment. A common indicator or predictor of colloidal stability of a protein molecule in a solution is the diffusion co-efficient ($k_D$) value, measured by dynamic light scattering (DLS) technique. The higher the diffusion co-efficient value, the more the repulsive forces, more solubility and less aggregate formation in the protein molecule, and thus the protein exhibits colloidal stability. And colloidal stability is an indicator of protein solubility, viscosity, type of protein aggregates etc.

Pharmaceutically acceptable excipients refer to the additives or carriers, which may contribute to stability of the antibody in formulation. The excipients may encompass stabilizers and tonicity modifiers. Examples of stabilizers and tonicity modifiers include, but not limited to, sugars, salts, surfactants, and derivatives and combination thereof.

Sugar/s herein includes sugars and sugar alcohols such as polyols. Sugars can be referred to monosaccharides, disaccharides, and polysaccharides. Examples of sugars include, but are not limited to, sucrose, trehalose, glucose, dextrose, raffinose and others. Examples of polyols include, but are not limited to, mannitol, sorbitol, and others.

Surfactant refers to pharmaceutically acceptable excipients used to protect the protein formulations against various stress conditions, like agitation, shearing, exposure to high temperature etc. The suitable surfactants include but are not limited to polyoxyethylensorbitan fatty acid esters such as Tween 20™ or Tween 80™, polyoxyethylene-polyoxypropylene copolymer (e.g. Poloxamer, Pluronic), sodium dodecyl sulphate (SDS) and the like or combination thereof.

Examples of salts include, but not limited to, sodium chloride, potassium chloride, magnesium chloride, sodium thiocyanate, ammonium thiocyanate, ammonium sulfate, ammonium chloride, calcium chloride, zinc chloride and/or sodium acetate.

Certain specific aspects and embodiments of the invention are more fully described by reference to the following examples. However, these examples should not be construed as limiting the scope of the invention in any manner.

Detailed Description of the Embodiments

The present invention discloses a stable pharmaceutical formulation of a fusion protein comprising buffer, sugar, amino acid and surfactant.

In one embodiment, the invention discloses a stable pharmaceutical formulation of a CTLA4-Ig fusion protein comprising buffer, sugar, amino acid and surfactant.

In one embodiment, the invention discloses a stable pharmaceutical formulation of a CTLA4-Ig fusion protein comprising buffer, sugar, histidine and surfactant, wherein the formulation is also devoid of arginine or lysine or glycine or proline or methionine.

In one embodiment, the invention discloses a stable pharmaceutical formulation of a CTLA4-Ig fusion protein comprising buffer, sugar, histidine and surfactant, and wherein the formulation does not require any other amino acids, that are commonly employed to stabilize a therapeutic protein formulation.

In any of the above embodiments, the sugar is sucrose or mannitol.

In the above said embodiments, the concentration of sugar present in the formulation is less than about 125 mg/ml, preferably about 100 mg/ml or about 90 mg/ml, or about 80 mg/ml, and the concentration of amino acid present in the formulation is less than about 20 mg/ml, preferably less than 15 mg/ml, and more preferably 10 mg/ml.

In any of the above said embodiments, the concentration of fusion protein in the formulation is about 10 mg/ml to 200 mg/ml, preferably 20 mg/ml to 150 mg/ml, more preferably 25 mg/ml to 125 mg/ml.

In any of the above said embodiments, viscosity of the CTLA4-Ig fusion protein formulation is less than 20 cp, preferably less than 10 cp, more preferably less than 5 cp.

In any of the above mentioned embodiments of the invention, the pH of CTLA4-Ig fusion protein formulation is from 6.0-8.0, preferably 6.5 to 7.5.

In any of the above mentioned embodiments of the invention, the sugars in the formulation can be sucrose, trehalose, sorbitol or mannitol or combinations thereof.

In the above said embodiments, the buffer mentioned in the formulation is an organic buffer, inorganic buffer and/or combinations thereof.

In any of the above mentioned embodiment of the invention, the said organic buffer is a citrate buffer, succinate buffer or acetate buffer.

In yet another embodiment of the invention, the inorganic buffer mentioned in the formulation is a phosphate buffer.

In any of the above said embodiment, the formulation optionally contains pharmaceutically acceptable excipients such as salts.

In an embodiment, the invention discloses a stable pharmaceutical formulation of CTLA4-Ig fusion protein comprising phosphate buffer, sugar, histidine and surfactant, wherein the ratio of the fusion protein to sugar is 1:0.8 or lower.

In the above mentioned embodiment, the ratio of the fusion protein to amino acid is 1:0.1 or lower.

In the above mentioned embodiment, the ratio of the CTLA4-Ig fusion protein to sugar to amino acid (eg., 1:0.7:0.1) results in comparable stability of the fusion protein, even under stress conditions, to the CTLA4-Ig formulation comprising higher sugar ratio in the fusion protein formulation (i.e., ratio of fusion protein to sugar being 1:1.3 or higher).

In an embodiment, the invention discloses a stable pharmaceutical formulation of CTLA4-Ig fusion protein comprising phosphate buffer, sucrose, histidine and surfactant.

In another embodiment, the invention discloses a stable fusion protein formulation comprising CTLA4-Ig fusion protein molecule, phosphate buffer, mannitol, histidine and surfactant.

In the above mentioned embodiments, the said stable formulation contains less than 10% of the protein in aggregate form when stored at 30° C. for four weeks.

In any of the above said embodiments, the formulation does not require arginine or lysine or glycine or proline or methionine. More specifically, in any of the above said embodiments, the formulation does not require any other amino acid/s, other than histidine.

In an embodiment, the invention discloses a stable pharmaceutical formulation of CTLA4-Ig fusion protein molecule comprising, citrate-phosphate buffer, mannitol, histidine and surfactant.

In an embodiment, the invention discloses a stable pharmaceutical formulation of CTLA4-Ig fusion protein molecule comprising, 125 mg/ml of CTLA4-Ig fusion protein, phosphate buffer, 75 mg/ml of mannitol, 15 mg/ml of histidine and 8 mg/ml of poloxamer.

In an embodiment, the invention discloses a stable pharmaceutical formulation of CTLA4-Ig fusion protein molecule comprising, 125 mg/ml of CTLA4-Ig fusion protein, phosphate buffer, 85 mg/ml of mannitol, 10 mg/ml of histidine and 8 mg/ml of poloxamer.

In an embodiment, the invention discloses a stable pharmaceutical formulation of CTLA4-Ig fusion protein molecule comprising, 125 mg/ml of CTLA4-Ig fusion protein, phosphate buffer, 100 mg/ml of sucrose, 10 mg/ml of histidine and 8 mg/ml of poloxamer.

In an embodiment, the invention discloses a method of obtaining a stable formulation of CTLA4-Ig fusion protein comprising addition of buffer, sugar, histidine and surfactant, and wherein histidine and sugar are also added to the pre-formulation process step of tangential flow filtration, performed as ultra-filtration [UF] and diafiltration [DF] and ultra-filtration, commonly performed for the concentration of the protein and buffer exchange.

In another embodiment, the invention discloses a method of increasing the stability of the CTLA4-Ig fusion protein composition, wherein the method comprises addition of histidine and sugar during the process step, in particular in the tangential flow filtration step [performed as ultrafiltration (UF) and diafiltration (DF) for product concentration and buffer exchange]. More particularly, the histidine and sugar are added to the buffer used in the diafiltration step.

In yet another embodiment, the invention discloses a method of increasing the stability of CTLA4-Ig fusion protein comprising steps of expression and purification of CTLA4-Ig fusion protein; followed by concentration and/or buffer exchange of the protein by UF-DF-UF, wherein the buffer used in any of the UF-DF-UF step includes histidine and sugar; and followed by formulation of the protein in a buffer comprising histidine, sugar and surfactant; wherein the stability of the protein is increased compared to the formulation of the protein that was processed by UF-DF-UF steps without the inclusion of histidine and sugar in any of its buffer.

In an embodiment, the invention discloses a method of preparing a stable high concentration CTLA4-Ig fusion protein formulation comprising;
  a) obtaining purified CTLA4-Ig fusion protein molecule from a chromatographic step
  b) subjecting CTLA4-Ig fusion protein obtained from step a) to ultrafiltration [UF] to concentrate the protein
  c) subjecting the concentrated CTLA4-Ig fusion protein obtained from step b) to diafiltration using a buffer comprising sugar and histidine and,
  d) subjecting the CTLA4-Ig fusion protein molecule from step c) to second ultrafiltration to obtain further and highly concentrated CTLA4-Ig fusion protein drug substance, wherein the concentration of formulation obtained in step d) is up to 200 mg/ml and is found to be stable as measured by the standard stability studies.

The stability of the protein molecule is found to be significantly increased in thermal and colloidal stability, when histidine and sugar components are added in the tangential flow filtration step. And addition of histidine and sugar in the UF or DF step, results in a stable product with % HMW being consistently less than 10, even after being subjected to accelerated stability studies.

In the above mentioned embodiment, the drug substance obtained from the above process is stable and drug product prepared from the drug substance is stable under accelerated stability conditions, wherein the concentration of the drug product is up to 140 mg/ml, preferably 130 mg/ml. The addition of histidine and sugar during DF step of TFF process helps in achieving stable and soluble higher concentrations of CTLA4-Ig fusion protein molecule (up to ~200 mg/ml) which in turn helps in preparation of desired concentration of drug product at commercial scale by simple dilution technique. This additionally saves time and resource.

In the above said embodiments, where histidine and sugar are also added to the pre-formulation process steps of UF or DF, the formulated protein contains less than 10% of the protein in aggregate form, even when stored at 30° C. for at least two weeks.

In another embodiment, the invention discloses a stable fusion protein formulation comprising CTLA4-Ig fusion protein molecule, phosphate buffer, sucrose, histidine, sodium chloride and surfactant.

In any of the above said embodiments, the formulation is devoid of specifically arginine and/or lysine.

In an embodiment, the invention discloses a method of reducing aggregation in CTLA4-Ig fusion protein formulation (upon storage) comprising addition of histidine and sugar to the fusion protein formulation.

In a further embodiment, the invention discloses a method of inhibiting fragmentation in CTLA4-Ig fusion protein formulation (upon storage) comprising addition of histidine and sugar to the formulation.

In another embodiment, the invention discloses a method to maintain colloidal stability of CTLA4-Ig fusion protein in a formulation comprising addition of histidine and sugar to the formulation containing the fusion protein.

In another embodiment, the invention discloses a method of reducing oxidation of CTLA4-Ig fusion protein in a formulation, wherein the method comprises addition of amino acid and sugar, wherein the amino acid is histidine. The combination of histidine and sugar protects methionine residues present in CTLA4-Ig fusion protein molecule from oxidation.

In the above said embodiment, the said stable formulation optionally contains an anti-oxidant.

In any of the above embodiments of the invention, the stable formulation is a liquid/aqueous formulation and is suitable for, and can be lyophilized as lyophilized powders. Further, the lyophilized formulation of CTLA4-Ig fusion protein can be reconstituted with appropriate diluent to achieve the liquid formulation suitable for administration.

In any of the above mentioned embodiments, the CTLA4-Ig fusion protein is abatacept or belatacept.

In any of the above said embodiments, the amino acid histidine added to the formulation, functions as a stabilizer and does not form part of a buffering agent.

In any of the above mentioned embodiments, the formulation of CTLA4-Ig fusion protein is a stable liquid (aqueous) formulation, which can be used for parenteral administration. Parenteral administration includes intravenous, subcutaneous, intra peritoneal, intramuscular-administration or any other route of delivery generally considered to be falling under the scope of parenteral administration and as is well known to a skilled person.

The disclosed formulations of the invention uses lesser amounts of sugar or sugar alcohol to stabilize the therapeutic fusion protein molecule. And the disclosed formulations of CTLA4-Ig fusion protein formulations comprising buffer, sugar, amino acid and surfactant are stable and can withstand multiple freeze thaw cycles and also agitation induced stress.

The disclosed formulation of the fusion protein, CTLA4-Ig is stabilized majorly by histidine and sugar combination and does not require any other amino acids such as arginine, lysine, proline, glycine or methionine, that are commonly used to stabilize a therapeutic formulation. Surprisingly, addition of any other amino acid or the combinations of amino acids to the formulation, indeed destabilizes the protein. CTLA4-Ig (eg., abatacept) being a fusion protein and dimeric in nature is a complex molecule, prone to aggregation and oxidation, is however unexpectedly stabilized only by the amino acid histidine (and sugar).

EXAMPLES

CTLA4-Ig fusion protein molecule, abatacept, suitable for storage in the present pharmaceutical composition is produced by standard methods known in the art. For example, abatacept is prepared by recombinant expression of CTLA4 fused with CH2 and CH3 portion of human IgG in a mammalian host cell such as Chinese Hamster Ovary cells. Further, the expressed abatacept is harvested and the crude harvest is subjected to standard downstream process steps that include purification, filtration and optionally dilution or concentration steps. For example, the crude harvest of abatacept may be purified using standard chromatography techniques such as affinity chromatography, ion-exchange chromatography and combinations thereof. The purified abatacept solution can additionally be subjected to one or more filtration steps, and the solution obtained is subjected to further formulation studies.

Example 1: Screening and Selection of Suitable Buffer to Formulate Abatacept

To select suitable buffer/s for stabilizing abatacept, various buffers were prepared. 40 mg/ml of abatacept in phosphate buffer back ground obtained from downstream chromatographic process was buffer exchanged and diluted to 25 mg/ml in the respective different buffer back ground/s. Details of the formulations are given in Table 1.

All abatacept formulations were subjected for accelerated stability studies at 25° C. and 40° C. for four weeks. Post which, the samples were analyzed for high molecular weight (HMW) species and low molecular weight (LMW) species [results are shown Table 2 and 3] using size exclusion chromatography (SEC) and also checked for change in pH [Table 4] and visual inspection [Table 5].

TABLE 1

Compositions of various abatacept formulations in different buffers as per example 1

| Sample Name | Composition |
| --- | --- |
| Aba-IV-1 | Abatacept 25 mg/ml, 10 mM phosphate buffer, pH 7.2 |
| Aba-IV-2 | Abatacept 25 mg/ml, 20 mM histidine buffer, pH 7.1 |
| Aba-IV-3 | Abatacept 25 mg/ml, 20 mM citrate buffer, pH 7.1 |
| Aba-IV-4 | Abatacept 25 mg/ml, 20 mM histidine-phosphate 7 buffer, pH.1 |
| Aba-IV-5 | Abatacept 25 mg/ml, 20 mM succinate buffer, pH 7.1 |
| Aba-IV-6 | Abatacept 25 mg/ml, 20 mM sodium-acetate buffer, pH 7.2 |

TABLE 2

SEC data of abatacept (25 mg/ml) formulations prepared as per example 1

High Molecular Weight (HMW) Species

| Sample Name | T0 0 W | 40° C. | | | | | 25° C. | | | |
|---|---|---|---|---|---|---|---|---|---|---|
| | | 1 W | 2 W | 4 W | Δ 2 W | Δ 4 W | 2 W | 4 W | Δ 2 W | Δ 4 W |
| Aba-IV-1 | 26.7 | 34.9 | 37.4 | 40.4 | 10.7 | 13.7 | 29.1 | 29.7 | 2.4 | 3.0 |
| Aba-IV-2 | 26.2 | 75.9 | 77.7 | 55.8 | 51.5 | 29.6 | 28.2 | 28.6 | 2.1 | 2.4 |
| Aba-IV-3 | 27.3 | 41.7 | 41.2 | 40.4 | 13.9 | 13.1 | 32.5 | 32.5 | 5.2 | 5.2 |
| Aba-IV-4 | 27.0 | 64.1 | 50.9 | 42.8 | 23.9 | 15.8 | 30.2 | 30.9 | 3.2 | 3.9 |
| Aba-IV-5 | 27.3 | 51.4 | 43.0 | 39.0 | 15.7 | 11.7 | 29.3 | 29.1 | 2.0 | 1.8 |
| Aba-IV-6 | 26.8 | 35.2 | 37.3 | 35.4 | 10.5 | 8.6 | 28.7 | 29.8 | 1.9 | 3.0 |

W—indicates weeks,
T0—indicates 'zero' time point,
Δ (delta) indicates change in a value from zero time point to a specified time point

TABLE 3

SEC data of abatacept (25 mg/ml) formulations prepared as per example 1

Low Molecular Weight (LMW) Species

| Sample Name | T0 0 W | 40° C. | | | | | 25° C. | | | |
|---|---|---|---|---|---|---|---|---|---|---|
| | | 1 W | 2 W | 4 W | Δ 2 W | Δ 4 W | 2 W | 4 W | Δ 2 W | Δ 4 W |
| Aba-IV-1 | 0.0 | 0.3 | 0.3 | 0.6 | 0.3 | 0.6 | 0.1 | 0.3 | 0.1 | 0.3 |
| Aba-IV-2 | 0.0 | 0.1 | 0.2 | 3.4 | 0.2 | 3.4 | 0.0 | 0.0 | 0.0 | 0.0 |
| Aba-IV-3 | 0.0 | 0.6 | 1.3 | 0.8 | 1.3 | 0.8 | 0.0 | 0.0 | 0.0 | 0.0 |
| Aba-IV-4 | 0.0 | 0.4 | 3.7 | 7.1 | 3.7 | 7.1 | 0.1 | 0.0 | 0.1 | 0.0 |
| Aba-IV-5 | 0.0 | 0.5 | 2.6 | 1.7 | 2.6 | 1.7 | 8.0 | 9.8 | 8.0 | 9.8 |
| Aba-IV-6 | 0.0 | 0.2 | 0.3 | 3.6 | 0.3 | 3.6 | 0.2 | 0.6 | 0.2 | 0.6 |

W—indicates weeks,
T0—indicates 'zero' time point,
Δ (delta) indicates change in a value from zero time point to a specified time point

TABLE 4 pH of abatacept (25 mg/ml) formulations prepared as per example 1 at 40° C. and 25° C.

| Sample Name | T0 0 W | 40° C. | | 25° C. | |
|---|---|---|---|---|---|
| | | 4 W | Δ pH | 4 W | Δ pH |
| Aba-IV-1 | 7.1 | 7.3 | 0.2 | 7.3 | 0.2 |
| Aba-IV-2 | 6.8 | 8.1 | 1.3 | 6.7 | 0.1 |
| Aba-IV-3 | 7.1 | 8.5 | 1.4 | 8.6 | 1.5 |
| Aba-IV-4 | 6.8 | 7.9 | 1.1 | 8.0 | 1.2 |
| Aba-IV-5 | 6.9 | 8.6 | 1.7 | 8.6 | 1.7 |
| Aba-IV-6 | 7.3 | 7.5 | 0.2 | 7.4 | 0.1 |

W-indicates weeks, T0-indicates 'zero' time point, Δ (delta) indicates change in a value from zero time point to a specified time point

TABLE 5

Visual inspection data of abatacept (25 mg/ml) formulations prepared as per example 1

| Sample Name | T0 0 W | 40° C. | | 25° C. | |
|---|---|---|---|---|---|
| | | 2 W | 4 W | 2 W | 4 W |
| Aba-IV-1 | Clear | Clear | Clear | Clear | Clear |
| Aba-IV-2 | Clear | Clear | Clear | Clear | Clear |
| Aba-IV-3 | Clear | Slightly opalescent | Slightly opalescent | opalescent | opalescent |
| Aba-IV-4 | Clear | opalescent | opalescent | opalescent | opalescent |
| Aba-IV-5 | Clear | opalescent | opalescent | opalescent | opalescent |
| Aba-IV-6 | Clear | Clear | Slightly opalescent | Clear | Clear |

W-indicates weeks, T0-indicates 'zero' time point

Example 2: High Concentration Abatacept (~125 mg/ml) Formulations in Presence of Sugar(s) and Amino Acid(s)

Approximately 120 mg/ml of abatacept in phosphate buffer back ground obtained from tangential flow filtration (TFF) step of downstream process was buffer exchanged in the respective buffer back ground. Post which, various excipients such as sugars and amino acids were added to high concentration abatacept formulations in different combinations and concentrations. Details of the formulations are given in Table 6. FDA approved subcutaneous formulation of abatacept contains phosphate buffer, 170 mg/ml of sucrose and poloxamer.

Hence, to maintain a reference standard, to ~120 mg/ml of in-house abatacept in phosphate buffer back ground, 170 mg/ml sucrose and 8 mg/ml of poloxamer were added to the formulation.

All high concentration abatacept formulations were subjected for accelerated stability studies at 30° C. for four weeks. Post which, the samples were analyzed for high molecular weight (HMW) species [results are shown Table 7] using size exclusion chromatography (SEC) and also checked for change in pH [Table 8] and visual inspection [Table 9].

TABLE 7

SEC data of high concentration abatacept (~120 mg/ml) formulations prepared as per example 2

| Sample Name | High molecular weight (HMW) species at 30° C. | | | | | |
|---|---|---|---|---|---|---|
| | 0 W | 1 W | 2 W | 4 W | Δ 2 W | Δ 4 W |
| Aba-Ref | 1.4 | 19.6 | 37.6 | NM | 36.2 | — |
| Aba-SC-1 | 2.4 | 5.8 | 17.3 | 34.4 | 14.9 | 32.0 |
| Aba-SC-2 | 2.4 | 7.0 | 15.2 | 30.0 | 12.8 | 27.6 |
| Aba-SC-3 | 2.4 | 5.4 | 23.6 | 41.2 | 21.2 | 38.8 |
| Aba-SC-4 | 2.5 | 4.7 | 6.9 | 10.3 | 4.4 | 7.9 |
| Aba-SC-5 | 2.4 | 4.7 | 10.7 | 30.2 | 8.3 | 27.7 |
| Aba-SC-6 | 2.4 | 13.3 | 28.1 | 39.7 | 25.7 | 37.3 |
| Aba-SC-7 | 2.4 | 6.5 | 12.5 | 24.5 | 10.1 | 22.1 |
| Aba-SC-8 | 2.3 | 4.6 | 14.8 | 27.3 | 12.5 | 25.0 |
| Aba-SC-9 | 2.4 | 7.4 | 23.3 | 32.3 | 20.8 | 29.9 |
| Aba-SC-10 | 2.4 | 5.3 | 7.9 | 18.5 | 5.5 | 16.2 |
| Aba-SC-11 | 2.4 | 6.0 | 12.3 | 26.3 | 9.9 | 23.9 |
| Aba-SC-12 | 2.5 | 5.2 | 11.3 | 23.1 | 8.8 | 20.6 |

W—indicates weeks;
NM—not measured since sample turned completely turbid,
Δ (delta) indicates change in a value from zero time point to a specified time point

TABLE 6

Compositions of various high concentration abatacept formulations (~120 mg/ml) prepared as example 2

| Sample Name | Composition |
|---|---|
| Aba-Ref | Abatacept 120 mg/ml, 8 mM phosphate buffer, 170 mg/ml of sucrose, 8 mg/ml poloxamer pH 6.8-7.2 |
| Aba-SC-1 | Abatacept 120 mg/ml, 10 mM phosphate buffer, 125 mg/ml of sucrose, 5 mg/ml lysine, 10 mg/ml glycine, 10 mg/ml arginine, 10 mg/ml histidine, 8 mg/ml poloxamer, pH 7.2 |
| Aba-SC-2 | Abatacept 120 mg/ml, 10 mM phosphate buffer, 125 mg/ml of sucrose, 10 mg/ml glycine, 10 mg/ml arginine, 10 mg/ml histidine, 8 mg/ml poloxamer, pH 7.2 |
| Aba-SC-3 | Abatacept 120 mg/ml, 10 mM phosphate buffer, 125 mg/ml of sucrose, 10 mg/ml glycine, 10 mg/ml arginine, 8 mg/ml poloxamer, pH 7.2 |
| Aba-SC-4 | Abatacept 120 mg/ml, 10 mM phosphate buffer, 125 mg/ml of sucrose, 10 mg/ml histidine, 8 mg/ml poloxamer, pH 7.2 |
| Aba-SC-5 | Abatacept 120 mg/ml, 10 mM phosphate buffer, 125 mg/ml of mannitol, 5 mg/ml lysine, 10 mg/ml glycine, 10 mg/ml arginine, 10 mg/ml histidine, 8 mg/ml poloxamer, pH 7.2 |
| Aba-SC-6 | Abatacept 120 mg/ml, 10 mM phosphate buffer, 125 mg/ml of trehalose, 5 mg/ml lysine, 10 mg/ml glycine, 10 mg/ml arginine, 10 mg/ml histidine, 8 mg/ml poloxamer, pH 7.2 |
| Aba-SC-7 | Abatacept 120 mg/ml, 10 mM phosphate buffer, 125 mg/ml of sorbitol, 5 mg/ml lysine, 10 mg/ml glycine, 10 mg/ml arginine, 10 mg/ml histidine, 8 mg/ml poloxamer, pH 7.2 |
| Aba-SC-8 | Abatacept 120 mg/ml, 10 mM phosphate buffer, 115 mg/ml of sorbitol, 5 mg/ml lysine, 10 mg/ml glycine, 10 mg/ml arginine, 10 mg/ml histidine, 8 mg/ml poloxamer, pH 7.2 |
| Aba-SC-9 | Abatacept 120 mg/ml, 10 mM phosphate buffer, 115 mg/ml of mannitol, 5 mg/ml lysine, 10 mg/ml glycine, 10 mg/ml arginine, 10 mg/ml histidine, 8 mg/ml poloxamer, pH 7.2 |
| Aba-SC-10 | Abatacept 120 mg/ml, 10 mM phosphate buffer, 100 mg/ml of sucrose, 5 mg/ml lysine, 10 mg/ml glycine, 10 mg/ml arginine, 10 mg/ml histidine, 8 mg/ml poloxamer, pH 7.2 |
| Aba-SC-11 | Abatacept 120 mg/ml, 20 mM phosphate-citrate buffer, 125 mg/ml of sucrose, 5 mg/ml lysine, 10 mg/ml glycine, 10 mg/ml arginine, 10 mg/ml histidine, 8 mg/ml poloxamer, pH 7.2 |
| Aba-SC-12 | Abatacept 120 mg/ml, 20 mM phosphate-citrate buffer, 125 mg/ml of mannitol, 5 mg/ml lysine, 10 mg/ml glycine, 10 mg/ml arginine, 10 mg/ml histidine, 8 mg/ml poloxamer, pH 7.2 |

TABLE 8 pH of high concentration abatacept formulations prepared as per example 2 at 30° C.

| Sample Name | pH at 30° C. | | |
|---|---|---|---|
| | 0 W | 4 W | Δ pH |
| Aba-Ref | 6.9 | 5.5 | −1.4 |
| Aba-SC-1 | 7.1 | 6.2 | −1.1 |
| Aba-SC-2 | 7.1 | 7.7 | 0.6 |
| Aba-SC-3 | 6.6 | 6.4 | −0.2 |
| Aba-SC-4 | 7.1 | 7.0 | −0.1 |
| Aba-SC-5 | 7.1 | 7.7 | 0.6 |
| Aba-SC-6 | 7.1 | 6.0 | −1.1 |
| Aba-SC-7 | 7.2 | 6.4 | −0.8 |
| Aba-SC-8 | 7.1 | 6.3 | −0.8 |
| Aba-SC-9 | 7.2 | 6.0 | −1.2 |
| Aba-SC-10 | 7.2 | 6.1 | −1.1 |
| Aba-SC-11 | 7.2 | 7.9 | 0.7 |
| Aba-SC-12 | 7.2 | 6.5 | −0.7 |

W-indicates weeks; Δ (delta) indicates change in a value from zero time point to a specified time point

TABLE 9

Visual inspection data of abatacept (25 mg/ml) formulations prepared as per example 2

| Sample Name | Visual Inspection 30° C. | | |
|---|---|---|---|
| | 0 W | 2 W | 4 W |
| Aba-Ref | Clear | Opalescent | Turbid |
| Aba-SC-1 | Clear | Opalescent | Opalescent |
| Aba-SC-2 | Clear | Opalescent | Clear |
| Aba-SC-3 | Clear | Clear | Opalescent |
| Aba-SC-4 | Clear | Opalescent | Clear |
| Aba-SC-5 | Clear | Clear | Clear |
| Aba-SC-6 | Clear | Opalescent | Opalescent |
| Aba-SC-7 | Clear | Clear | Opalescent |
| Aba-SC-8 | Clear | Opalescent | Opalescent |
| Aba-SC-9 | Clear | Opalescent | Opalescent |
| Aba-SC-10 | Clear | Clear | Opalescent |
| Aba-SC-11 | Clear | Clear | clear |
| Aba-SC-12 | Clear | Opalescent | Opalescent |

W-indicates weeks

Example 3: High Concentration Abatacept (~125 mg/ml) Formulations

Approximately 120 mg/ml of abatacept in phosphate buffer back ground obtained from tangential flow filtration (TFF) step of downstream process was buffer exchanged in the respective buffer back ground. Post which, various excipients such as sugars, amino acids and sodium chloride were added to high concentration abatacept formulations in different combinations and concentrations. Details of the formulations are given in Table 10. FDA approved subcutaneous formulation of abatacept contains phosphate buffer, 170 mg/mi of sucrose and poloxamer. Hence, to maintain a reference standard, to ~120 mg/mi of in-house abatacept in phosphate buffer back ground, 170 mg/mi sucrose and 8 mg/ml of poloxamer were added to the formulation.

All high concentration abatacept formulations were subjected for accelerated stability studies at 30 SC for two weeks. Post which, the samples were analyzed for high molecular weight (HMW) species and active dimer form [results are shown Table 11] using size exclusion chromatography (SEC) and also checked for change in pH [Table 12] and visual inspection [Table 13].

Light scattering of protein samples at 333 nm were also checked using nano drop and results are represented in Table 14.

TABLE 10

Compositions of various high concentration abatacept formulations prepared as per example 3

| Sample Name | Composition |
|---|---|
| Aba-Ref | 120 mg/ml of Abatacept, phosphate buffer, 170 mg/ml of sucrose, 8 mg/ml Poloxamer pH 6.8-7.2 |
| Aba-SC-13 | 120 mg/ml of Abatacept, phosphate buffer, 10 mg/ml histidine, 8 mg/ml poloxamer, pH 7.2 |
| Aba-SC-14 | 120 mg/ml of Abatacept, phosphate buffer, 15 mg/ml histidine, 8 mg/ml poloxamer, pH 7.2 |
| Aba-SC-15 | 120 mg/ml of Abatacept, phosphate buffer, 10 mg/ml arginine, 8 mg/ml poloxamer, pH 7.2 |
| Aba-SC-16 | 120 mg/ml of Abatacept, phosphate buffer, 10 mg/ml histidine, 10 mg/ml arginine, 10 mM NaCl, 8 mg/ml poloxamer, pH 7.2 |
| Aba-SC-17 | 120 mg/ml of Abatacept, phosphate buffer, 125 mg/ml of sucrose, 10 mg/ml histidine, 8 mg/ml poloxamer, pH 7.2 |
| Aba-SC-18 | 120 mg/ml of Abatacept, phosphate buffer, 125 mg/ml of sucrose, 15 mg/ml histidine, 8 mg/ml poloxamer, pH 7.2 |
| Aba-SC-19 | 120 mg/ml of Abatacept, phosphate buffer, 125 mg/ml of sucrose 10 mg/ml histidine, 10 mg/ml arginine, 10 mM NaCl, 8 mg/ml poloxamer, pH 7.2 |
| Aba-SC-20 | 120 mg/ml of Abatacept, phosphate buffer, 125 mg/ml of sucrose, 10 mg/ml histidine, 10 mM NaCl, 8 mg/ml poloxamer, pH 7.2 |
| Aba-SC-21 | 120 mg/ml of Abatacept, citrate-phosphate buffer, 125 mg/ml of mannitol, 10 mg/ml histidine, 8 mg/ml poloxamer, pH 7.2 |

TABLE 11

SEC data of dimer content of abatacept (~120 mg/ml) formulations prepared as per example 3

| Sample Name | Dimer content at 30° C. | | | High molecular weight species at 30° C. | | | Low molecular weight species at 30° C. | | |
|---|---|---|---|---|---|---|---|---|---|
| | 0 W | 1 W | 2 W | 0 W | 1 W | 2 W | 0 W | 1 W | 2 W |
| Aba-Ref | 97.8 | 92.9 | 88.7 | 2.2 | 7.1 | 11.0 | 0.0 | 0.0 | 0.3 |
| Aba-SC-13 | 97.6 | 84.8 | 75.2 | 2.4 | 15.2 | 24.8 | 0.0 | 0.0 | 0.0 |
| Aba-SC-14 | 97.7 | 85.6 | 68.2 | 2.3 | 14.4 | 31.7 | 0.0 | 0.0 | 0.2 |
| Aba-SC-15 | 97.6 | 89.2 | 71.3 | 2.3 | 13.0 | 28.6 | 0.0 | 0.0 | 0.2 |
| Aba-SC-16 | 97.6 | 83.0 | 74.8 | 2.4 | 17.0 | 25.2 | 0.0 | 0.0 | 0.0 |
| Aba-SC-17 | 97.6 | 92.4 | 86.8 | 2.4 | 7.6 | 13.2 | 0.0 | 0.0 | 0.0 |
| Aba-SC-18 | 97.7 | 92.6 | 88.2 | 2.3 | 7.4 | 11.8 | 0.0 | 0.0 | 0.0 |
| Aba-SC-19 | 97.7 | 89.7 | 79.7 | 2.3 | 10.3 | 20.1 | 0.0 | 0.0 | 0.2 |
| Aba-SC-20 | 97.8 | 91.6 | 85.1 | 2.2 | 8.4 | 14.9 | 0.0 | 0.0 | 0.0 |
| Aba-SC-21 | 97.7 | 94.4 | 92.6 | 2.3 | 5.6 | 7.5 | 0.0 | 0.0 | 0.0 |

W-indicates weeks

TABLE 12 pH of high concentration abatacept formulations prepared as per example 3 at 30° C.

| Sample Name | pH at 30° C. | | | Δ pH at 2 W |
|---|---|---|---|---|
| | 0 W | 1 W | 2 W | |
| Aba-Ref | 7.0 | 6.8 | 6.8 | −0.2 |
| Aba-SC-13 | 7.3 | 7.1 | 7.2 | −0.1 |
| Aba-SC-14 | 7.4 | 7.2 | 7.2 | −0.2 |
| Aba-SC-15 | 6.9 | 6.8 | 6.8 | −0.1 |
| Aba-SC-16 | 7.3 | 7.2 | 7.2 | −0.1 |
| Aba-SC-17 | 7.3 | 7.1 | 7.1 | −0.2 |
| Aba-SC-18 | 7.4 | 7.2 | 7.2 | −0.2 |
| Aba-SC-19 | 7.3 | 7.4 | 8.0 | 0.6 |
| Aba-SC-20 | 7.4 | 7.2 | 7.3 | −0.1 |
| Aba-SC-21 | 7.5 | 7.4 | 7.4 | −0.1 |

W-indicates weeks; Δ (delta) indicates change in a value from zero time point to a specified time point

TABLE 13

Visual inspection data of high concentration abatacept formulations prepared as per example 3 at 30° C.

| Sample Name | Visual Inspection 30° C. | | |
|---|---|---|---|
| | 0 W | 1 W | 2 W |
| Aba-Ref | Clear, colorless | Clear, colorless | Clear, colorless |
| Aba-SC-13 | Clear, colorless | Clear, colorless | Clear, colorless |
| Aba-SC-14 | Clear, colorless | Clear, colorless | Clear, colorless |
| Aba-SC-15 | Clear, colorless | Clear, colorless | Clear, colorless |
| Aba-SC-16 | Clear, colorless | Clear, colorless | Clear, colorless |
| Aba-SC-17 | Clear, colorless | Clear, colorless | Clear, colorless |
| Aba-SC-18 | Clear, colorless | Clear, colorless | Clear, colorless |
| Aba-SC-19 | Clear, colorless | Clear, colorless | Clear, colorless |
| Aba-SC-20 | Clear, colorless | Clear, colorless | Clear, colorless |
| Aba-SC-21 | Clear, colorless | Clear, colorless | Clear, colorless |

TABLE 14

Light scattering data at 333 nm (A333) of high concentration abatacept formulations prepared as per example 3 at 30° C.

| Sample Name | Light scattering data at 30° C. | | |
|---|---|---|---|
| | 0 W | 1 W | 2 W |
| Aba-Ref | 0.1 | 0.1 | 0.2 |
| Aba-SC-13 | 0.0 | 0.2 | 0.4 |
| Aba-SC-14 | 0.0 | 0.2 | 0.1 |
| Aba-SC-15 | 0.0 | 0.1 | 0.0 |
| Aba-SC-16 | 0.1 | 0.1 | 0.0 |
| Aba-SC-17 | 0.0 | 0.1 | 0.1 |
| Aba-SC-18 | 0.0 | 0.1 | 0.3 |
| Aba-SC-19 | 0.0 | 0.1 | 0.3 |
| Aba-SC-20 | 0.1 | 0.1 | 0.0 |
| Aba-SC-21 | 0.1 | 0.1 | 0.0 |

Example 4: Addition of Excipients During Tangential Flow Filtration (TFF) Step for Stability of High Concentration CTLA4-Ig Fusion Proteins In example 2 and 3, purified abatacept obtained from the downstream chromatographic step was further buffer exchanged into phosphate buffer and concentrated by tangential flow filtration (TFF), performed as a series of ultrafiltration, diafiltration and ultrafiltration steps. Post which, excipients were added to the formulation. However, differing from this conventional strategy, various sugars such as sucrose and mannitol and amino acid such as histidine and glycine were incorporated during the TFF itself (i.e., before the formulation step or before formulating the protein as a drug product). 8-15 mg/ml concentration of abatacept fusion protein in acetate buffer obtained from chromatographic step was subjected for ultrafiltration to concentrate up to 60 mg/ml. Post which, the samples were subjected for diafiltration wherein the diafiltration medium contained phosphate buffer (formulation buffer) with excipients such as sugars and amino acid(s), and in another separate experiment, the diafiltration medium without sugar and amino acid(s) in the phosphate buffer was experimented. Post diafiltration, the samples were subjected for second ultrafiltration to concentrate up to 180 mg/ml to 200 mg/ml. These high concentration samples were found to be stable without any visible particles/aggregates. The highly concentrated samples were further diluted to 125 mg/ml and some of the excipients such as sugars, surfactant and optionally amino acid such as glycine was added to prepare a final formulation. 8 mg/ml of poloxamer was added to all final formulations. Details of the formulations are given in Table 15. All the samples were subjected for accelerated stability studies at 30° C. for 2 weeks. The samples were analyzed for high molecular weight (HMW) species and active dimer form [results are shown Table 16] using size exclusion chromatography (SEC) and also checked for change in pH [Table 17] and visual inspection [Table 18].

TABLE 15

Compositions of various high concentration abatacept formulations prepared as per example 4

| Sample Name | Formulation buffer composition during TFF | Formulation composition after TFF |
|---|---|---|
| Aba-SC-22 | 20 mM phosphate buffer | 125 mg/ml of Abatacept, 20 mM phosphate buffer, 8 mg/ml poloxamer, pH 7.2 |

TABLE 15-continued

Compositions of various high concentration abatacept formulations prepared as per example 4

| Sample Name | Formulation buffer composition during TFF | Formulation composition after TFF |
| --- | --- | --- |
| Aba-SC-23 | 20 mM phosphate buffer and 75 mg/ml Sucrose | 125 mg/ml of Abatacept, 20 mM phosphate buffer, 170 mg/ml sucrose, 8 mg/ml poloxamer, pH 7.2 |
| Aba-SC-24 | 20 mM phosphate buffer and 170 mg/ml Sucrose | 125 mg/ml of Abatacept, 20 mM phosphate buffer, 170 mg/ml sucrose, 8 mg/ml poloxamer, pH 7.2 |
| Aba-SC-25 | 20 mM phosphate buffer and 75 mg/ml Sucrose | 125 mg/ml of Abatacept, 20 mM phosphate buffer, 100 mg/ml sucrose, 10 mg/ml lysine, 0.58 mg/ml NaCl, 8 mg/ml poloxamer, pH 7.2 |
| Aba-SC-26 | 20 mM phosphate buffer, 100 mg/ml sucrose, 10 mg/ml histidine | 125 mg/ml of Abatacept, 20 mM phosphate buffer, 100 mg/ml sucrose, 10 mg/ml histidine, 8 mg/ml poloxamer, pH 7.2 |
| Aba-SC-27 | 20 mM phosphate buffer, 100 mg/ml sucrose, 10 mg/ml histidine, 10 mg/ml glycine | 125 mg/ml of Abatacept, 20 mM phosphate buffer, 100 mg/ml sucrose, 10 mg/ml histidine, 10 mg/ml glycine, 8 mg/ml poloxamer, pH 7.2 |
| Aba-SC-28 | 20 mM phosphate buffer, 100 mg/ml sucrose, 10 mg/ml histidine, 10 mg/ml glycine | 125 mg/ml of Abatacept, 20 mM phosphate buffer, 100 mg/ml sucrose, 10 mg/ml histidine, 10 mg/ml glycine, 8 mg/ml poloxamer, 0.58 mg/ml NaCl, pH 7.2 |
| Aba-SC-29 | 20 mM phosphate buffer, 75 mg/ml mannitol | 125 mg/ml of Abatacept, 20 mM phosphate buffer, 75 mg/ml mannitol, 6.6 mg/ml ammonium sulphate, 8 mg/ml poloxamer, pH 7.2 |
| Aba-SC-30 | 20 mM phosphate buffer, 75 mg/ml mannitol | 125 mg/ml of Abatacept, 20 mM phosphate buffer, 75 mg/ml mannitol, 10 mg/ml histidine, 6.6 mg/ml ammonium sulphate, 8 mg/ml poloxamer, pH 7.2 |
| Aba-SC-31 | 20 mM phosphate buffer, 75 mg/ml mannitol | 125 mg/ml of Abatacept, 20 mM phosphate buffer, 100 mg/ml mannitol, 15 mg/ml histidine, 8 mg/ml poloxamer, pH 7.2 |
| Aba-SC-32 | 20 mM phosphate buffer, 75 mg/ml mannitol | 125 mg/ml of Abatacept, 20 mM phosphate buffer, 100 mg/ml mannitol, 10 mg/ml lysine, 8 mg/ml poloxamer, pH 7.2 |
| Aba-SC-33 | 20 mM phosphate buffer, 75 mg/ml mannitol | 125 mg/ml of Abatacept, 20 mM phosphate buffer, 100 mg/ml mannitol, 10 mg/ml Glycine, 8 mg/ml poloxamer, pH 7.2 |
| Aba-SC-34 | 20 mM phosphate buffer; 75 mg/ml mannitol, 10 mg/ml histidine | 125 mg/ml of Abatacept, 20 mM phosphate buffer, 75 mg/ml mannitol, 10 mg/ml histidine, 8 mg/ml poloxamer, pH 7.2 |
| Aba-SC-35 | 20 mM phosphate buffer; 75 mg/ml mannitol, 15 mg/ml histidine | 125 mg/ml of Abatacept, 20 mM phosphate buffer, 75 mg/ml mannitol, 15 mg/ml histidine, 8 mg/ml poloxamer, pH 7.2 |
| Aba-SC-36 | 20 mM phosphate buffer; 75 mg/ml mannitol, 10 mg/ml histidine | 125 mg/ml of Abatacept, 20 mM phosphate buffer, 75 mg/ml mannitol, 10 mg/ml histidine, 5 mg/ml glycine, 8 mg/ml poloxamer, pH 7.2 |
| Aba-SC-37 | 20 mM phosphate buffer; 75 mg/ml mannitol, 15 mg/ml histidine | 125 mg/ml of Abatacept, 20 mM phosphate buffer, 75 mg/ml mannitol, 15 mg/ml histidine, 5 mg/ml glycine, 8 mg/ml poloxamer, pH 7.2 |
| Aba-SC-38 | 20 mM phosphate buffer; 85 mg/ml mannitol, 10 mg/ml histidine | 125 mg/ml of Abatacept, 20 mM phosphate buffer, 85 mg/ml mannitol, 10 mg/ml histidine, 8 mg/ml poloxamer, pH 7.2 |
| Aba-SC-39 | 20 mM phosphate buffer; 85 mg/ml mannitol, 10 mg/ml histidine | 125 mg/ml of Abatacept, 20 mM phosphate buffer, 85 mg/ml mannitol, 10 mg/ml histidine, 5 mg/ml glycine, 8 mg/ml poloxamer, pH 7.2 |
| Aba-SC-40 | 20 mM phosphate buffer; 85 mg/ml mannitol, 15 mg/ml histidine | 125 mg/ml of Abatacept, 20 mM phosphate buffer, 85 mg/ml mannitol, 15 mg/ml histidine, 8 mg/ml poloxamer, pH 7.2 |
| Aba-SC-41 | 20 mM phosphate buffer, 75 mg/ml mannitol, 10 mg/ml histidine | 125 mg/ml of Abatacept, 20 mM phosphate buffer, 75 mg/ml mannitol, 15 mg/ml histidine, 10 mg/ml proline, 8 mg/ml poloxamer, pH 7.2 |
| Aba-SC-42 | 20 mM phosphate buffer, 75 mg/ml mannitol, 10 mg/ml histidine | 125 mg/ml of Abatacept, 20 mM phosphate buffer, 75 mg/ml mannitol, 10 mg/ml histidine, 10 mg/ml proline, 8 mg/ml poloxamer, pH 7.2 |

TABLE 16

SEC data of high concentration abatacept formulations prepared as per example 4

| Sample Name | Dimer content at 30° C. | | High molecular weight species at 30° C. | | Low molecular weight species at 30° C. | |
|---|---|---|---|---|---|---|
| | 0 W | 2 W | 0 W | 2 W | 0 W | 2 W |
| Aba-SC-22 | 98.6 | 59.7 | 1.4 | 37.6 | 0 | 2.7 |
| Aba-SC-23 | 98.6 | 87.6 | 1.4 | 12.4 | 0 | 0 |
| Aba-SC-24 | 98.9 | 94.3 | 1.1 | 5.7 | 0 | 0 |
| Aba-SC-25 | 98.7 | 75.8 | 1.3 | 24.2 | 0 | 0 |
| Aba-SC-26 | 98.9 | 91.8 | 1.1 | 8.2 | 0 | 0 |
| Aba-SC-27 | 98.9 | 92.4 | 1.1 | 7.6 | 0 | 0 |
| Aba-SC-28 | 98.8 | 92.2 | 1.2 | 7.8 | 0 | 0 |
| Aba-SC-29 | 98.2 | 87.3 | 1.8 | 12.6 | 0 | 0.1 |
| Aba-SC-30 | 98.3 | 89.2 | 1.7 | 10.6 | 0 | 0.1 |
| Aba-SC-31 | 98.9 | 89.4 | 1.1 | 10.6 | 0 | 0 |
| Aba-SC-32 | 98.9 | 84.3 | 1.1 | 15.7 | 0 | 0 |
| Aba-SC-33 | 98.9 | 88.2 | 1.2 | 11.9 | 0 | 0 |
| Aba-SC-34 | 98.8 | 91.2 | 1.2 | 8.8 | 0 | 0 |
| Aba-SC-35 | 98.9 | 92.0 | 1.1 | 8.1 | 0 | 0 |
| Aba-SC-36 | 98.8 | 91.7 | 1.2 | 8.3 | 0 | 0 |
| Aba-SC-37 | 98.9 | 92.4 | 1.1 | 7.6 | 0 | 0 |
| Aba-SC-38 | 98.9 | 91.7 | 1.1 | 8.3 | 0 | 0 |
| Aba-SC-39 | 98.9 | 92.0 | 1.1 | 8.0 | 0 | 0 |
| Aba-SC-40 | 98.8 | 92.3 | 1.2 | 7.7 | 0 | 0 |
| Aba-SC-41 | 99.0 | 93.0 | 1.0 | 7.0 | 0 | 0 |
| Aba-SC-42 | 99.0 | 87.5 | 1.0 | 12.5 | 0 | 0 |

W—indicates weeks

TABLE 17 pH of high concentration abatacept formulations prepared as per example 4 at 30° C.

| Sample Name | pH at 30° C. | | |
|---|---|---|---|
| | 0 W | 2 W | Δ pH |
| Aba-SC-22 | 6.9 | 6.1 | −0.8 |
| Aba-SC-23 | 7.0 | 6.9 | −0.1 |
| Aba-SC-24 | 7.1 | 7.2 | 0.1 |
| Aba-SC-25 | 6.8 | 6.8 | 0 |
| Aba-SC-26 | 7.0 | 7.1 | 0.1 |
| Aba-SC-27 | 7.0 | 7.1 | 0.1 |
| Aba-SC-28 | 7.0 | 7.0 | 0 |
| Aba-SC-29 | NT | NT | — |
| Aba-SC-30 | NT | NT | — |
| Aba-SC-31 | 7.4 | 7.3 | −0.1 |
| Aba-SC-32 | 6.8 | 6.8 | 0 |
| Aba-SC-33 | 7.0 | 6.9 | −0.1 |
| Aba-SC-34 | 7.0 | 7.1 | 0.1 |
| Aba-SC-35 | 7.1 | 7.2 | 0.1 |
| Aba-SC-36 | 7.0 | 7.1 | 0.1 |
| Aba-SC-37 | 7.1 | 7.2 | 0.1 |
| Aba-SC-38 | 7.0 | 7.1 | 0.1 |
| Aba-SC-39 | 7.0 | 7.1 | 0.1 |
| Aba-SC-40 | 7.1 | 7.2 | 0.1 |
| Aba-SC-41 | 7.4 | 7.4 | 0 |
| Aba-SC-42 | 7.3 | 7.2 | −0.1 |

W-indicates weeks; NT-Not tested due to sample constrain; Δ (delta) indicates change in a value from zero time point to a specified time point

TABLE 18

Visual inspection data of high concentration abatacept formulations prepared as per example 4 at 30° C.

| Sample Name | Visual Inspection at 30° C. | |
|---|---|---|
| | 0 W | 2 W |
| Aba-SC-22 | Clear | Turbid |
| Aba-SC-23 | Clear, colorless, no visible particles | Clear, colorless, no visible particles |
| Aba-SC-24 | Clear, colorless, no visible particles | Clear, colorless, no visible particles |
| Aba-SC-25 | Clear, colorless, no visible particles | Clear, colorless, no visible particles |
| Aba-SC-26 | Clear, colorless, no visible particles | Clear, colorless, no visible particles |
| Aba-SC-27 | Clear, colorless, no visible particles | Clear, colorless, no visible particles |
| Aba-SC-28 | Clear, colorless, no visible particles | Clear, colorless, no visible particles |
| Aba-SC-29 | Clear, colorless, no visible particles | Clear, colorless, no visible particles |
| Aba-SC-30 | Clear | Opalescent |
| Aba-SC-31 | Clear, colorless, no visible particles | Clear, colorless, no visible particles |
| Aba-SC-32 | Clear, colorless, no visible particles | Clear, colorless, no visible particles |
| Aba-SC-33 | Clear, colorless, no visible particles | Clear, colorless, no visible particles |
| Aba-SC-34 | Clear, colorless, no visible particles | Clear, colorless, no visible particles |
| Aba-SC-35 | Clear, colorless, no visible particles | Clear, colorless, no visible particles |
| Aba-SC-36 | Clear, colorless, no visible particles | Clear, colorless, no visible particles |
| Aba-SC-37 | Clear, colorless, no visible particles | Clear, colorless, no visible particles |
| Aba-SC-38 | Clear, colorless, no visible particles | Clear, colorless, no visible particles |
| Aba-SC-39 | Clear, colorless, no visible particles | Clear, colorless, no visible particles |
| Aba-SC-40 | Clear, colorless, no visible particles | Clear, colorless, no visible particles |
| Aba-SC-41 | Clear, colorless, no visible particles | Clear, colorless, no visible particles |
| Aba-SC-42 | Clear, colorless, no visible particles | Clear, colorless, no visible particles |

W-indicates weeks;

Viscosity of some of the abatacept formulations prepared as per example 4 were measured using m-VROC® viscometer. Results are given Table 19.

TABLE 19

Viscosity of high concentration abatacept formulations

| Sample Name | Viscosity (mPa/S) |
|---|---|
| Aba-SC-24 | 10.9 |
| Aba-SC-26 | 9.2 |
| Aba-SC-34 | 9.0 |
| Aba-SC-38 | 9.0 |

Alternatively, the amino acid methionine was added to the abatacept formulation of histidine and sugar combination and was evaluated for an effect on stability. The samples (with and without methionine in the formulation) were subjected for accelerated stability studies at 30° C. for one week. The samples were analyzed for high molecular weight (HMW) species and active dimer form [results are shown Table 20] using size exclusion chromatography (SEC).

TABLE 20

SEC data of abatacept formulations prepared with and without methionine molecular

| Sample | | Dimer content at 30° C. | | High molecular weight species at 30° C. | |
|---|---|---|---|---|---|
| Name | Composition | '0' W | '1' W | '0' W | '1' W |
| Aba-SC-38 | 125 mg/ml of Abatacept, 20 mM phosphate buffer, 85 mg/ml mannitol, 10 mg/ml histidine, 8 mg/ml poloxamer, pH 7.2 | 1.3 | 5.0 | 98.7 | 95.0 |
| Aba-SC-43 | 125 mg/ml of Abatacept, 20 mM phosphate buffer, 85 mg/ml mannitol, 10 mg/ml histidine, 10 mM methionine, 8 mg/ml poloxamer, pH 7.2 | 1.4 | 4.9 | 98.6 | 95.1 |

W-indicates weeks

Example 5: Long Term Stability Data of High Concentration Abatacept Formulations From the above experiments, it is evident that addition of sugar and amino acid/(s) during TFF plays a significant role in stabilizing abatacept. Hence, further some of the formulations from the above experiment were further observed till 4 weeks at 30° C. The samples were analyzed for high molecular weight (HMW) species and active dimer form [results are shown Table 21 using size exclusion chromatography (SEC).

TABLE 21

SEC data of high concentration abatacept formulations prepared as per example 4 at 30° C. for four weeks.

| Sample | Dimer content at 30° C. | | High molecular weight species at 30° C. | | Low molecular weight species at 30° C. | |
|---|---|---|---|---|---|---|
| Name | 0 W | 4 W | 0 W | 4 W | 0 W | 4 W |
| Aba-SC-34 | 98.8 | 85.9 | 1.2 | 14.1 | 0 | 0 |
| Aba-SC-35 | 98.9 | 87.0 | 1.1 | 13.0 | 0 | 0 |
| Aba-SC-36 | 98.8 | 86.7 | 1.2 | 13.3 | 0 | 0 |
| Aba-SC-37 | 98.9 | 87.9 | 1.1 | 12.1 | 0 | 0 |
| Aba-SC-38 | 98.9 | 86.7 | 1.1 | 13.3 | 0 | 0 |
| Aba-SC-39 | 98.9 | 87.1 | 1.1 | 13.0 | 0 | 0 |
| Aba-SC-40 | 98.8 | 87.6 | 1.2 | 12.4 | 0 | 0 |

W—indicates weeks;

Abatacept formulations (A' (125 mg/ml abatacept, 100 mg/ml sucrose, 15 mg/ml histidine, 10 mg/ml glycine and 8 mg/ml polaxamer) and B' (125 mg/ml abatacept, 75 mg/ml mannitol, 15 mg/ml histidine, 10 mg/ml glycine and 8 mg/ml polaxamer) were subjected to accelerated stability studies at 30° C. for four weeks, post which a CD28 receptor ligand based assay was performed to demonstrate and prove that the stable abatacept formulation is functionally active. The formulations were found to be functionally active and exhibited 90.7% of potency (A') and 93.6% of potency (B').

Example 6: Assessment of Oxidation of High Concentration Abatacept Formulations Some of the abatacept fusion protein formulations prepared as per example 4 were subjected for mass spectrometry to understand the effective of excipients on oxidation sites of abatacept. Abatacept fusion protein contains seven methionine residues. A few of the Abatacept formulations containing sugar and amino acid/s from example 4, which were subjected for accelerated stability studies till four weeks at 30° C. for four weeks collected at '0' and four weeks' time point. The abatacept formulations collected at '0' and '4' week time point at 30° C. were subjected for denaturation using a buffer (8.2 M guanidine hydrochloride, 1 mM EDTA and 0.1 M Tris, pH 7.5), and reduced using 10 mM Dithiothreitol and alkylated using iodoacetamide. The alkylated samples were subjected to PD-10 column to remove digestion buffer. The protein fractions obtained from PD-10 column were treated with trypsin and N-Glycanse at 37° C. for overnight. The peptide fragments obtained from the above step was subjected for mass spectrometry to understand the effect of excipients on oxidized sites of abatacept. The result of the study is given Table 22 and the % of oxidation demonstrates that the methionine residues are protected from oxidation

TABLE 22

Percentage oxidation of methionine in abatacept formulations stored at 30° C.

| Sample Name | % Average oxidized methionine at T0 | % Average oxidized methionine at 30° C. for 4 weeks |
|---|---|---|
| Aba-SC-24 | 5.7 | 5.5 |
| Aba-SC-27 | 6.6 | 5.6 |
| Aba-SC-37 | 4.9 | 7.6 |

T0-inidcates data point at '0' time point.

The invention claimed is:
1. An aqueous pharmaceutical formulation of CTLA4-Ig fusion protein comprising CTLA4-Ig fusion protein, a buffer, sugar, histidine and surfactant, wherein the CTLA4-Ig fusion protein is abatacept or belatacept, and the formulation has a pH of 6.5-8.0, and wherein the weight ratio of CTLA4-Ig fusion protein to sugar is in a range of 1:0.8 to 1:0.6, and the weight ratio of the CTLA4-Ig fusion protein to histidine is in a range of 1:0.1 to 1:0.08.
2. The formulation according to claim 1, wherein the concentration of CTLA4-Ig fusion protein is about 20 mg/ml to about 200 mg/ml.

* * * * *